United States Patent [19]

Filippi, Jr. et al.

[11] Patent Number: Plant 5,790

[45] Date of Patent: Aug. 26, 1986

[54] ASPARAGUS FERN-SNOWFLAKE

[76] Inventors: John Filippi, Jr., 936 Cybus Way, Southampton, Pa. 18966; H. Bruce Hellerick, P.O. Box 86 Seitz Rd., Columbia, Pa. 17512

[21] Appl. No.: 658,155

[22] Filed: Oct. 5, 1984

[51] Int. Cl.[4] ..... A01H 5/00

[52] U.S. Cl. ..... Plt./88

[58] Field of Search ..... Plt./88

*Primary Examiner*—Robert E. Bagwill

[57] ABSTRACT

A new and distinct variety of Asparagus Fern, botanically known as *Asparagus sprengeri* is provided. The new variety is distinguished from the regular *Asparagus sprengeri* by a marked tendency to be variegated at an early stage of development.

1 Drawing Figure

SUMMARY OF THE INVENTION

The new and distinct variety of Asparagus Fern was discovered by John Filippi, Jr. in 1977 while growing in a large flat of several thousand regular *Asparagus sprengeri* seedlings (non-patented) growing at the Matt Haist and Associates in the Township of North Hampton, Greenhouse 4 at Warminster, Pa. At the time of John's discovery his attention was attracted to a single plant in the seedling block which was significantly different in appearance from all other plants in the block primarily because of its variegated growth characteristic. H. Bruce Hellerick, a trained horticulturalist, after discovery and observation of the plant noted its unusual characteristic and suggested that steps be taken to continue to observe the plant and protect it. The plant was first asexually reproduced at our direction during 1984 when the plant was divided into three plants. This asexual reproduction by division has confirmed that the distinctive characteristics of the new variety come true to form and are established and transmitted through succeeding propagations. This new variety of Asparagus Fern has been named Snowflake.

BRIEF DESCRIPTION OF THE PHOTOGRAPH

The Asparagus Fern illustrated is the original which was found by chance at Matt Haist and Associates July, 1977 prior to division in 1984. The color is depicted as nearly true as possible to make the same in a color illustration of this character. FIG. 1 illustrates the variegation, branching habit and general form of Asparagus Fern-Snowflake.

DETAILED DESCRIPTION OF THE NEW VARIETY

Unless otherwise stated the new variety has characteristics substantially identical to those of the regular *Asparagus sprengeri* fern (Non-patented). Color terminology used herein is to be accorded its usual dictionary significance. The variegation of the new variety is particularly evident at an early age. When the shoots first emerge from the crown they have a Deep Vinaceous color 2.5R 5.40/5.6 (Munsell). Then when the cladophylls (leaves) expand the variegation of white 8.0N 9.0/14.0 and green 7.0GY 4.0/12.5 (Munsell) becomes evident. At the same time the cladophylls are expanding the color of the shoots changes to Parrot Green 5.9GY 5.41/5.6 (Munsell). As the shoots elongate, underdeveloped spines emerge at the nodes as compared with the commonly exhibited sharp, fully developed, stiff spines of *Asparagus sprengeri* (non-patented).

The size of the mature *Asparagus sprengeri* cv Snowflake is approximately the same size as *Asparagus sprengeri* (non-patented).

We claim:

1. A new and distinct variety of *Asparagus sprengeri*, substantially as illustrated and described, characterized by its general similarity to the common *Asparagus sprengeri*, but being distinct therefrom by (1) a marked propensity to be variegated at an early age.

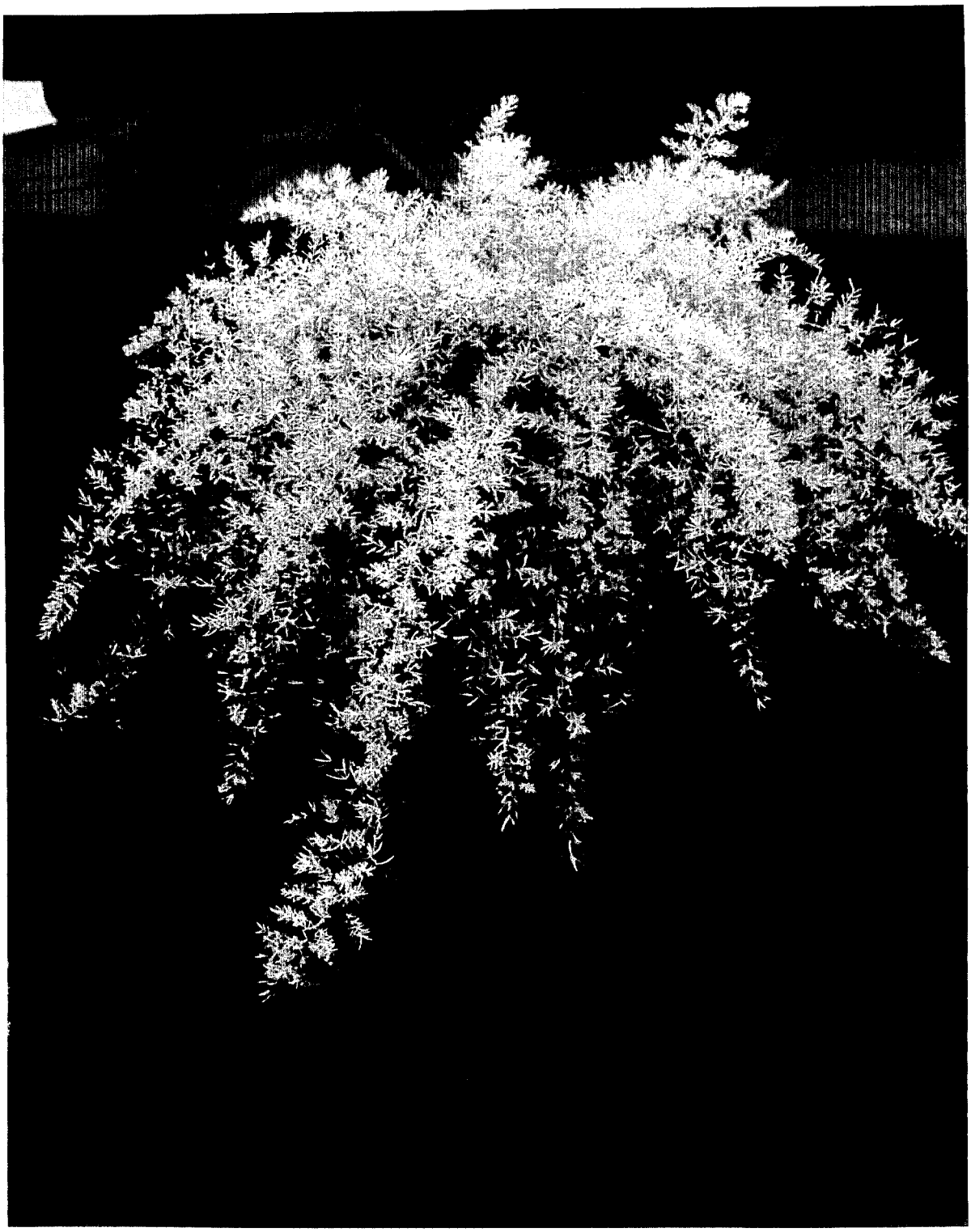

* * * * *